US00PP24180P2

(12) United States Plant Patent
Smaal

(10) Patent No.: US PP24,180 P2
(45) Date of Patent: Jan. 21, 2014

(54) ***VERONICA* PLANT NAMED 'AGRIVEROBLUE'**

(50) Latin Name: *Veronica spicata*
Varietal Denomination: Agriveroblue

(75) Inventor: André Smaal, De Kwakel (NL)

(73) Assignee: Agriom B.V., De Kwakel (NL)

( * ) Notice: Subject to any disclaimer, the term of this patent is extended or adjusted under 35 U.S.C. 154(b) by 0 days.

(21) Appl. No.: 13/507,241

(22) Filed: Jun. 14, 2012

(51) Int. Cl.
*A01H 5/00* (2006.01)

(52) U.S. Cl.
USPC ..... Plt./251

(58) Field of Classification Search
USPC ..... Plt./251
See application file for complete search history.

*Primary Examiner* — Kent L Bell
(74) *Attorney, Agent, or Firm* — C. A. Whealy

(57) ABSTRACT

A new and distinct cultivar of *Veronica* plant named 'Agriveroblue', characterized by its compact and upright plant habit; freely branching habit; early and freely flowering habit; dense inflorescences with numerous medium violet blue-colored flowers; and good container performance.

1 Drawing Sheet

Botanical designation: *Veronica spicata.*
Cultivar denomination: 'AGRIVEROBLUE'.

BACKGROUND OF THE INVENTION

The present invention relates to a new and distinct cultivar of *Veronica* plant, botanically known as *Veronica spicata* and hereinafter referred to by the name 'Agriveroblue'.

The new *Veronica* plant is a product of a planned breeding program conducted by the Inventor in De Kwakel, The Netherlands. The objective of the breeding program was to create new compact and freely branching *Veronica* plants with early and freely flowering habit.

The new *Veronica* plant originated from a cross-pollination made by the Inventor in June 2009 in De Kwakel, The Netherlands, of a proprietary selection of *Veronica spicata* identified as code number 208011, not patented, as the female, or seed, parent with a proprietary selection of *Veronica spicata* identified as code number 208004-02, not patented, as the male, or pollen, parent. The new *Veronica* plant was discovered and selected by the Inventor as a single flowering plant from within the progeny of the stated cross-pollination in a controlled greenhouse environment in De Kwakel, The Netherlands in January, 2010.

Asexual reproduction of the new *Veronica* plant by top cuttings in a controlled environment in De Kwakel, The Netherlands since March, 2010 has shown that the unique features of this new *Veronica* plant are stable and reproduced true to type in successive generations.

SUMMARY OF THE INVENTION

Plants of the new *Veronica* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Agriveroblue'. These characteristics in combination distinguish 'Agriveroblue' as a new and distinct *Veronica* plant:

1. Compact and upright plant habit.
2. Freely branching habit.
3. Early and freely flowering habit.
4. Vernalization treatment not required for flower initiation and development.
5. Dense inflorescences with numerous medium violet blue-colored flowers.
6. Good container performance.

Plants of the new *Veronica* differ primarily from plants of the female parent selection in the following characteristics:

1. Plants of the new *Veronica* are more compact than plants of the female parent selection.
2. Plants of the new *Veronica* flower earlier than plants of the female parent selection.

Plants of the new *Veronica* differ primarily from plants of the male parent selection in the following characteristics:

1. Plants of the new *Veronica* are more freely branching than plants of the male parent selection.
2. Plants of the new *Veronica* are more freely flowering than plants of the male parent selection.

Plants of the new *Veronica* can be compared to plants of *Veronica spicata* 'Yabblu', disclosed in U.S. Plant Pat. No. 19,304. In side-by-side comparisons conducted in De Kwakel, The Netherlands, plants of the new *Veronica* differed primarily from plants of 'Yabblu' in the following characteristics:

1. Plants of the new *Veronica* were more compact than plants of 'Yabblu'.
2. Plants of the new *Veronica* grew faster than plants of 'Yabblu'.
3. Plants of the new *Veronica* had larger leaves than plants of 'Yabblu'.
4. Plants of the new *Veronica* were more freely flowering than plants of 'Yabblu'.
5. Flowers of plants of the new *Veronica* were darker violet blue in color than flowers of plants of 'Yabblu'.
6. Plant habit of plants of the new *Veronica* was more suitable as a container plant than plant habit of plants of 'Yabblu'.

BRIEF DESCRIPTION OF THE PHOTOGRAPH

The accompanying colored photograph illustrates the overall appearance of the *Veronica* plant showing the colors as true as it is reasonably possible to obtain in colored reproductions of this type. Colors in the photograph may differ slightly from the color values cited in the detailed botanical description which accurately describe the actual colors of the new *Veronica* plant. The photograph comprises a side perspective view of a typical flowering plant of 'Agriveroblue' grown in a container.

DETAILED BOTANICAL DESCRIPTION

Plants used for the aforementioned photograph and following description were grown in 12-cm containers during the autumn and winter in a glass-covered greenhouse in De Kwakel, The Netherlands and under cultural practices which closely approximate commercial potted *Veronica* production. During the production of the plants, day temperatures averaged 19° C. and night temperatures averaged 17° C. Plants were pinched one week after planting and were 20 weeks old when the photograph and the description were taken. In the following description, color references are made to The Royal Horticultural Society Colour Chart, 2001 Edition, except where general terms of ordinary dictionary significance are used.

Botanical classification: *Veronica spicata* 'Agriveroblue'.

Parentage:

*Female, or seed, parent*.—Proprietary selection of *Veronica spicata* identified as code number 208011, not patented.

*Male, or pollen, parent*.—Proprietary selection of *Veronica spicata* identified as code number 208004-02, not patented.

Propagation:

*Type cutting*.—Top cuttings.

*Time to initiate roots, summer*.—About 14 days at 23° C. to 25° C.

*Time to initiate roots, winter*.—About 14 to 18 days at 21° C.

*Time to produce a rooted young plant, summer*.—About 21 days at 23° C. to 25° C.

*Time to produce a rooted young plant, winter*.—About 24 to 28 days at 21° C.

*Root description*.—Medium in thickness, fibrous; white to light grey brown in color.

*Rooting habit*.—Freely branching; medium density.

Plant description:

*Plant type*.—Herbaceous perennial.

*Plant and growth habit*.—Compact and upright plant habit, narrow inverted triangle; basal branching habit with about six primary lateral branches, pinching enhances lateral branch development; moderately vigorous growth habit; fast growth rate.

*Plant height*.—About 25 cm.

*Plant width*.—About 15 cm to 18 cm.

*Lateral branch description*.—Length: About 15 cm to 20 cm. Diameter: About 2.5 mm. Internode length: About 2.5 cm. Strength: Strong, sturdy. Texture: Finely pubescent. Color: Close to 139C.

Foliage description:

*Arrangement*.—Opposite, simple.

*Length*.—About 6 cm.

*Width*.—About 2 cm to 2.5 cm.

*Shape*.—Narrowly ovate.

*Apex*.—Acute.

*Base*.—Acuminate.

*Margin*.—Serrate.

*Texture, upper surface*.—Smooth, glabrous.

*Texture, lower surface*.—Pubescent.

*Venation pattern*.—Pinnate.

*Color*.—Developing leaves, upper surface: Close to 137D. Developing leaves, lower surface: Close to 139C. Fully expanded leaves, upper surface: Close to 137C; venation, close to 138B. Fully expanded leaves, lower surface: Close to 139C; venation, close to 138B.

*Petiole length*.—About 5 mm to 8 mm.

*Petiole diameter*.—About 1.5 mm to 2 mm.

*Petiole texture, upper and lower surfaces*.—Smooth, glabrous.

*Petiole color, upper and lower surfaces*.—Close to 139C.

Flower description:

*Flower arrangement and shape*.—Single campanulate flowers arranged on upright terminal racemes; racemes dense; flowers face outwardly.

*Flowering habit*.—Freely flowering, about 100 flowers per raceme and about 10 to 16 inflorescences developing per plant.

*Fragrance*.—None detected.

*Natural flowering season*.—During the spring and summer, plants begin flowering about 13 weeks after planting; during the autumn and winter, plants begin flowering about 17 weeks after planting; in the garden, plants flower naturally from May to August.

*Flower longevity on the plant*.—Individual flowers last about one week; flowers not persistent.

*Flower buds*.—Length: About 4 mm to 5 mm. Diameter: About 2 mm. Shape: Narrowly ovoid. Color: Close to 97C.

*Inflorescence height*.—About 7 cm.

*Inflorescence diameter*.—About 2 cm.

*Flower diameter*.—About 6 mm.

*Flower height*.—About 8 mm.

*Petals*.—Quantity and arrangement: Four in a single whorl, petals fused towards the base. Length: About 6 mm. Width: About 2.5 mm. Shape: Oblanceolate. Apex: Obtuse. Margin: Entire. Texture, upper and lower surfaces: Smooth, glabrous. Color: When opening, upper and lower surfaces: Close to 94C; towards the base, close to 97D. Fully opened, upper and lower surfaces: Close to 94B; towards the base, close to 97D.

*Sepals*.—Quantity and arrangement: Four in a single whorl, sepals fused towards the base. Length: About 3 mm to 5 mm. Width: About 1 mm. Shape: Narrowly elliptic. Apex: Acute. Margin: Entire. Texture, upper and lower surfaces: Smooth, glabrous. Color: When opening, upper surface: Close to 137B. When opening, lower surface: Close to 137C. Fully opened, upper surface: Close to 137A. Fully opened, lower surface: Close to 137B.

*Peduncles*.—Length, from uppermost leaves to base of raceme: About 8 mm. Diameter: About 2.5 mm. Aspect: Erect. Strength: Strong. Texture: Smooth, glabrous. Color: Close to 139C.

*Pedicels*.—Length: About 1 mm. Diameter: About 0.5 mm. Aspect: About 60° from peduncle axis. Strength: Strong. Texture: Smooth, glabrous. Color: Close to 139B.

*Reproductive organs*.—Stamens: Quantity per flower: Two. Anther length: About 1 mm to 1.5 mm. Anther shape: Elliptic. Anther color, immature: Close to 83C. Anther color, mature: Close to 93A. Pollen amount: Moderate. Color: Close to 160C. Pistils: Quantity per flower: One. Stigma shape: Filiform. Stigma color: Close to 93B. Style length: About 5.5 mm. Style color: Close to 93B. Ovary color: Close to 139C.

*Fruits*.—Length: About 3 mm. Diameter: About 3 mm. Texture: Smooth, glabrous. Color: Close to 144B.

*Seeds*.—Length: About 1 mm. Diameter: About 0.7 mm. Texture: Smooth, glabrous. Color: Close to 199C.

Disease & pest resistance: Plants of the new *Veronica* have not been noted to be resistant to pathogens and pests common to *Veronica* plants.

Temperature tolerance: Plants of the new *Veronica* have been observed to tolerate temperatures ranging from about −15° C. to 35° C.

It is claimed:

1. A new and distinct *Veronica* plant named 'Agriveroblue' as illustrated and described.

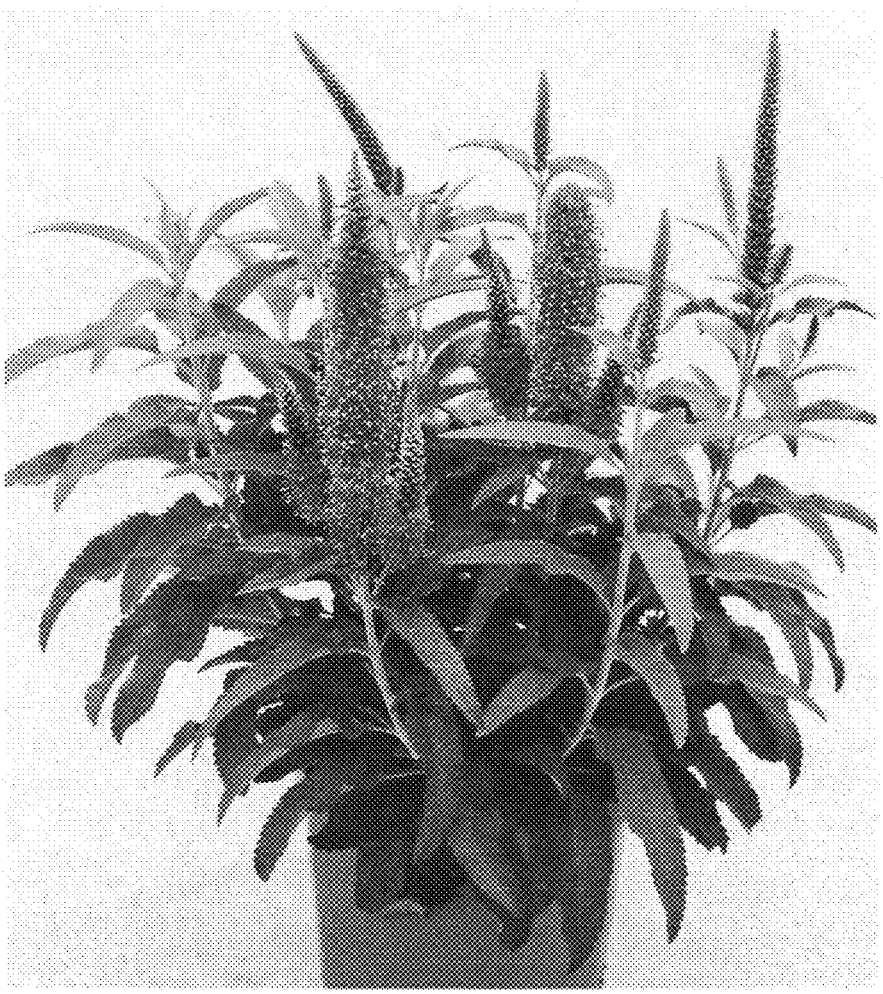

* * * * *